US00PP19882P2

(12) United States Plant Patent
Eggleton

(10) Patent No.: US PP19,882 P2
(45) Date of Patent: Mar. 31, 2009

(54) *VIOLA* PLANT NAMED 'SMEV1'

(50) Latin Name: *Viola×hybrida*
Varietal Denomination: SMEV1

(76) Inventor: Steven Eggleton, 3 Harris Road, Wonga Park, Melbourne, Victoria (AU), 3115

( * ) Notice: Subject to any disclaimer, the term of this patent is extended or adjusted under 35 U.S.C. 154(b) by 0 days.

(21) Appl. No.: 12/069,404

(22) Filed: Feb. 11, 2008

(51) Int. Cl.
*A01H 5/00* (2006.01)

(52) U.S. Cl. ..... Plt./323
(58) Field of Classification Search ..... Plt./323
See application file for complete search history.

(56) References Cited

PUBLICATIONS http://web.archive.org/web/20061203235748/http://www.e-seeds.com/c–3453–viola–blue–moon.aspx.*
http://web.archive.org/web/20060923074229/http://web.tiscali.co.uk/heartsease/nvps/bluemoon.htm.*

* cited by examiner

*Primary Examiner*—Annette H Para
*Assistant Examiner*—S. B. McCormick Ewoldt

(57) ABSTRACT

A new cultivar of *Viola* named 'SMEV1' that is distinguishable by compact habit, green glossy foliage, and large fragrant, blue and cream-white flowers. In combination these traits set 'SMEV1' apart from all other existing varieties of *Viola* known to the inventor.

2 Drawing Sheets

Genus: *VIOLA*.
Species: ×*hybrida*.
Denomination 'SMEV1'.

BACKGROUND OF THE INVENTION

The present invention relates to a new and distinct cultivar of violet grown for use in borders, containers, and the landscape. The new invention from the family *Violaceae*, is known botanically as *Viola×hybrida* and will be referred to hereinafter by the cultivar name 'SMEV1'.

The new *Viola* cultivar named 'SMEV1' resulted from a formal breeding program developed by the inventor and conducted in Wonga Park, Victoria, Australia. Goals of the breeding program were to produce a range of heat tolerant, perennial *Viola* exhibiting a range of flower color. The program was started in 2001. The inventor conducted deliberate controlled cross-pollination in October 2002. The seedlings that resulted from this cross were grown to maturity. Five seedlings were selected, asexually reproduced and grown to maturity for another two generations. From the final generation the inventor selected 'SMEV1' in September 2004, based on the criteria of flower size and flower color.

'SMEV1' is a selected hybrid seedling that resulted from cross-pollination of *Viola* 'Etain' (female parent, unpatented) and *Viola* 'Painted Porcelain' (male parent, unpatented). The new *Viola* cultivar named 'SMEV1' is distinguishable from the parents by a band of blue color that "bleeds" into a large area of the petal blade, onto a predominantly cream-white background. The flower of *Viola* 'Etain' exhibits a fine lavender edge on petals, with a yellow center. The flower of 'Painted Porcelain' has mauve venation spreading throughout petals and varying in color depth throughout season.

The distinguishing characteristics of 'SMEV1' are compact habit, glossy green foliage, large perfume-scented flowers held on short peduncles, with blue-margined flower color on a predominantly cream-white petal background. Mature dimensions are 20 cm. in height and 40 cm. in width. Cultural requirements include full sun to filtered light, moist organic soil, and regular water. Hardy to USDA Zone 5 and blooms early winter through spring.

The first asexual reproduction of 'SMEV1' was accomplished in 2004, by the inventor in a cultivated area of Victoria, Australia. The method used was softwood cuttings. Since that time 'SMEV1' has been determined stable and true to type in subsequent generations of asexual propagation.

SUMMARY OF THE INVENTION

The following traits have been repeatedly observed and represent the distinguishing characteristics of the new *Viola* cultivar named 'SMEV1'. These traits in combination distinguish 'SMEV1' from all other existing varieties of *Viola* known to the inventor. 'SMEV1' has not been tested under all possible conditions and phenotypic differences may be observed with variations in environmental, climatic, and cultural conditions, however, without any variance in genotype.

1. 'SMEV1' exhibits compact dome-shaped habit.
2. 'SMEV1' exhibits green glossy foliage.
3. 'SMEV1' exhibits large perfume-scented flowers on short peduncles.
4. 'SMEV1' exhibits blue-margined and cream-white flowers.
5. 'SMEV1' is 20 cm. in height and 40 cm. in width.
6. 'SMEV1' is hardy to USDA Zone 5.
7. 'SMEV1' blooms spring through fall.

BRIEF DESCRIPTION OF THE DRAWINGS

The accompanying color drawings illustrate the overall appearance of the new *Viola* cultivar named 'SMEV1' showing color as true as is reasonably possible to obtain in color reproductions of this type. Color in the drawings may differ from the color values cited in the detailed botanical description, which accurately describe the actual color of the new variety 'SMEV1'. Drawings were made in December 2007 of plants grown under glass in 1-liter containers.

The drawing labeled

The drawing labeled

Figure 1:
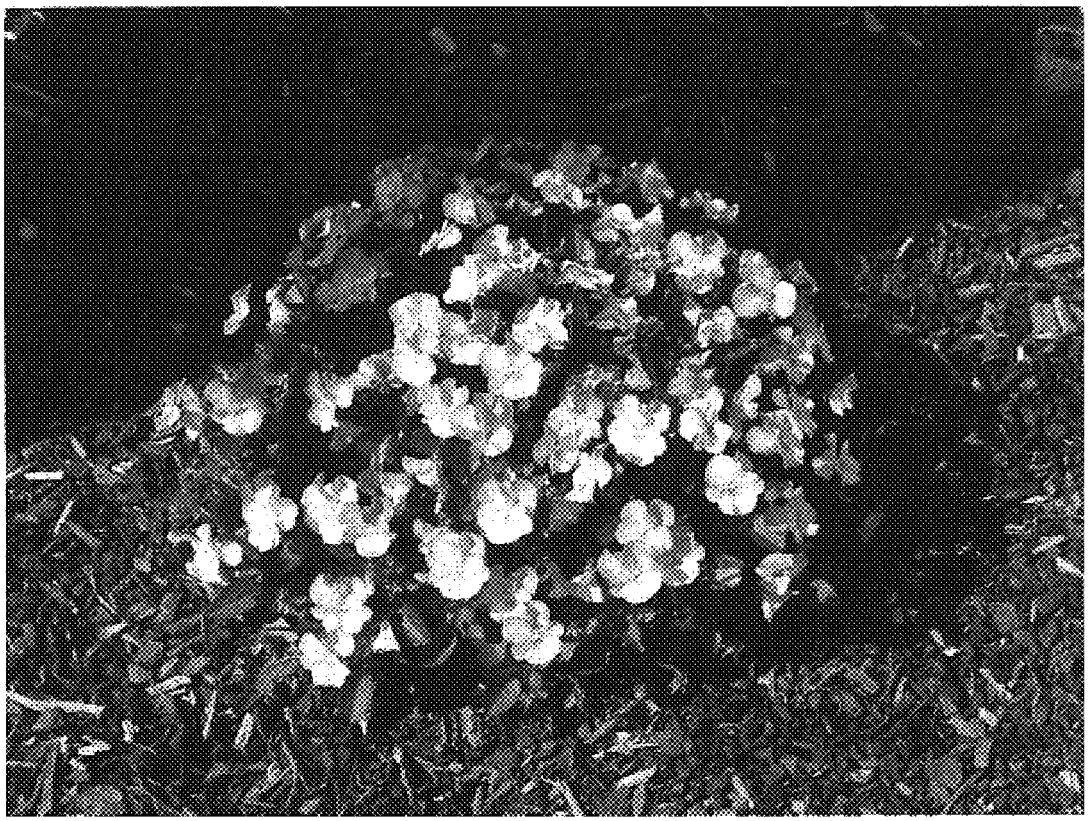
FIG. 1 depicts the entire plant in bloom.
Figure 2:
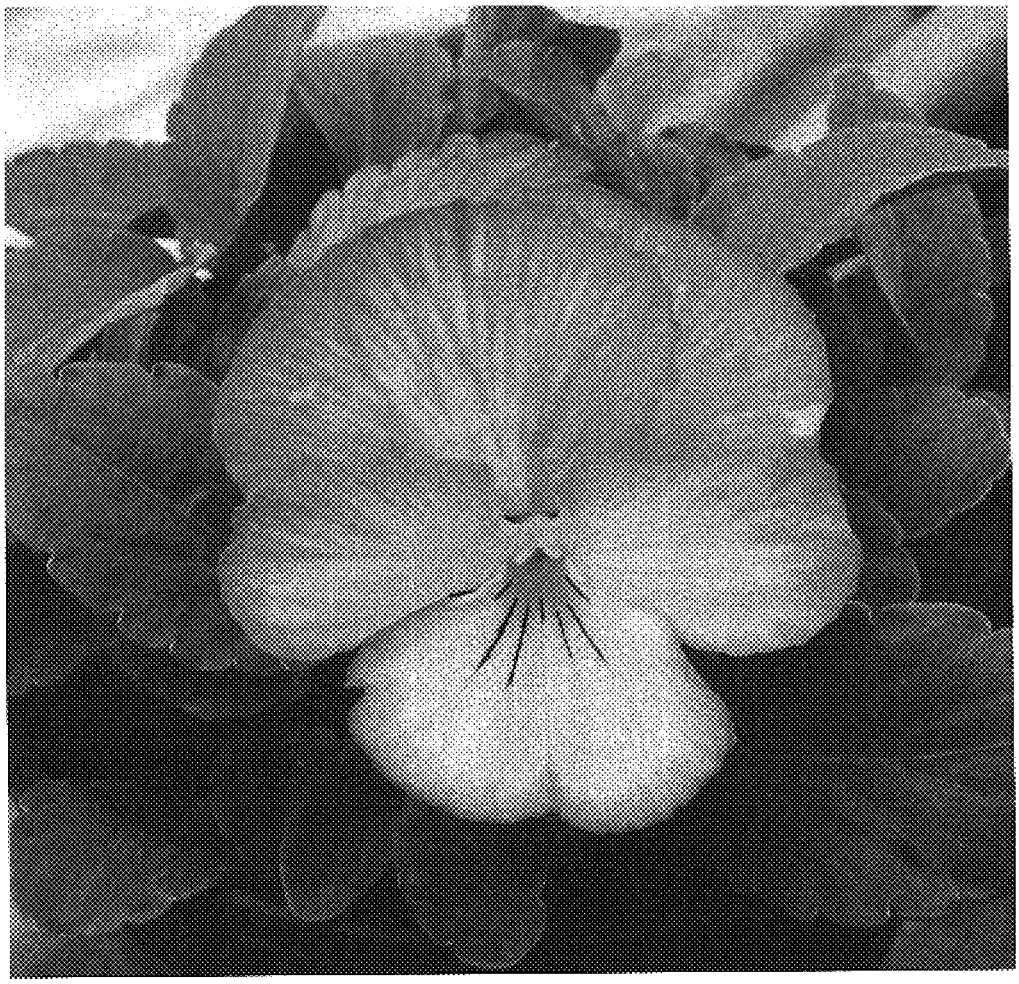
FIG. 2 depicts a close-up view of the flower.

Drawings were made using conventional techniques and although flower and foliage color may appear different from actual color due to light reflectance, they are as accurate as possible by conventional photography.

BOTANICAL DESCRIPTION OF THE PLANT

The following is a detailed botanical description of the new *Viola* cultivar named 'SMEV1'. Observations, measurements, values and comparisons were collected in Arroyo Grande, Calif. during the winter months, from 6-month-old plants grown indoors in 1-liter containers. Color determinations are made in accordance with The 2001 Royal Horticultural Society Colour Chart from London, England, except where general color terms of ordinary dictionary significance are used.

Botanical classification: *Viola×hybrida* 'SMEV1'.
Family: *Violaceae*.
Genus: *Viola*.
Species: *×hybrida*.
Denomination: 'SMEV1'.
Common name: Violet.
Habit: Compact dome.
Commercial category: Ornamental.
Use: Borders, container, and the landscape.
Suggested commercial container size: 1-liter container.
Parentage: *Viola×hybrida* 'SMEV1' is a selected hybrid seedling resulting from controlled deliberate cross-pollination of the following parents:
- *Female parent.*—*Viola* 'Etain' (non-patented).
- *Male parent.*—*Viola* 'Painted Porcelain' (non-patented).

Propagation method: Softwood cuttings/division.
Rooting system: Fine and fibrous.
Vigor: Moderate.
Time to develop roots (range): 14 to 20 days to develop roots on an initial cutting.
Temperature to develop roots (range): The recommended air temperature is 20–21° Centigrade.
Crop time (range): 4–6 months to produce a 1-liter container from a rooted cutting.
Plant height: 20 cm.
Plant width: 40 cm.
Cultural requirements: Grow in moist organic soil, shade to filtered sunlight with regular water.
Pest or disease resistance: No disease or pest resistance known to the inventor.
Hardiness: USDA Zone 5.
Stem:
- *Stem color.*—N138A.
- *Stem length* (*average*).—5 cm.
- *Stem width.*—0.40 cm.
- *Stem shape.*—Sulcate.
- *Stem surface.*—Glabrous.

Foliage:
- *Type.*—Evergreen.
- *Leaf arrangement.*—Alternate.
- *Leaf division.*—Simple.
- *Internode* (*average length*).—2 cm.
- *Margin.*—Crenate.
- *Leaf shape.*—Ovate.
- *Leaf length* (*average*).—5 cm.
- *Leaf width* (*average*).—3.50 cm.
- *Leaf color* (*abaxial surface*).—N138B.
- *Leaf color* (*adaxial surface*).—N138A.
- *Leaf base.*—Rounded.
- *Leaf apex.*—Rounded.
- *Venation.*—Pinnate.
- *Vein color* (*abaxial and adaxial surfaces*).—N138A.
- *Leaf surface* (*abaxial and adaxial*).—Glabrous.
- *Leaf attachment.*—Petiolate.
- *Petiole color.*—138A.
- *Petiole dimensions.*—3.75 cm. in length and 3 mm. in width.
- *Petiole shape.*—Sulcate.
- *Petiole surface.*—Glabrous.
- *Stipules.*—Present and persistent.
- *Stipule form.*—Leaf-like.
- *Stipule margin.*—Cleft.
- *Stipule apex.*—Rounded.
- *Stipule base.*—Truncate.
- *Stipule color.*—138A.
- *Stipule surface* (*abaxial and adaxial*).—Glabrous.
- *Stipule attachment.*—Sessile.
- *Stipule dimensions* (*average*).—2 cm. in length and 1 cm. in width.
- *Fragrance.*—None observed.

Inflorescence:
- *Inflorescence.*—Solitary flower.
- *Inflorescence quantity* (*range*).—15–20 on a 1-liter container plant.
- *Aspect.*—Facing upward and outward.
- *Inflorescence diameter.*—5.25 cm.
- *Inflorescence length.*—5.50 cm.
- *Inflorescence depth.*—3 cm.
- *Inflorescence arrangement.*—Terminal inflorescence.
- *Inflorescence color* (*abaxial and adaxial surfaces*).—92A, 158B and N88A are all individually present.
- *Inflorescence shape.*—Rotate.
- *Blooming seasons.*—Winter-spring.
- *Peduncle length* (*average*).—9 cm.
- *Peduncle width.*—5 mm.
- *Peduncle shape.*—Plano-convex.
- *Peduncle surface.*—Glabrous.
- *Peduncle color.*—138A.
- *Peduncle strength.*—Strong.
- *Bud color.*—N89A.
- *Bud surface.*—Glabrous.
- *Bud apex.*—Rounded.
- *Corolla tube depth.*—15 mm.
- *Petal quantity.*—5 petals.
- *Fused or unfused.*—Unfused.
- *Petal shape* (*range*).—Obdeltoid to obovate.
- *Petals fused or unfused.*—Unfused.
- *Petal apex* (*range*).—Obtuse to emarginate.
- *Petal base.*—Attenuate.
- *Petal margin* (*range*).—Crenulate to entire.
- *Petal length* (*range*).—2.75 cm. to 3 cm.
- *Petal width* (*range*).—2.50 cm. 4 cm.
- *Petal color* (*abaxial and adaxial surfaces*).—92A, 158B and N88A are all individually present.
- *Petal surface* (*abaxial and adaxial*).—Glabrous.
- *Calyx shape.*—Stellate.

*Calyx diameter.*—2.10 cm.
*Sepals.*—5 sepals.
*Fused or unfused.*—Sepals unfused.
*Sepal color* (*abaxial and adaxial surfaces*).—138A.
*Sepal apex.*—Acute.
*Sepal base.*—Auriculate.
*Sepal surface* (*abaxial and adaxial*).—Glabrous.
*Sepal margin.*—Entire.
*Sepal shape.*—Oblanceolate.
*Inflorescence self-cleaning or persistent.*—Self-cleaning.
*Inflorescence fragrance.*—Sweet perfume fragrance.
*Lastingness of inflorescence* (*range*).—3–4 days on or off the plant.

Reproductive organs:
*Stamen quantity.*—5 joined around ovary.
*Stamen length.*—4 mm.
*Stamen color.*—158A.
*Anther length.*—<1 mm.
*Anther color.*—162A.
*Pollen color.*—164A.
*Pollen quantity.*—Minimal.
*Pistil quantity.*—1.
*Pistil height.*—8.5 mm.
*Style height.*—1 mm.
*Style color.*—151A.
*Stigma dimensions.*—1.5 mm. in height and 1.5 mm. in diameter.
*Stigma color.*—151A.
*Stigma shape.*—Globular.
*Stigma surface.*—Glandular.
*Ovary position.*—Superior.
*Ovary color.*—151A.
*Ovary shape.*—Dome-shaped.
*Ovary dimensions.*—6 mm. in height and 4 mm. in width.

Seed: None observed to date.

What is claimed is:

1. A new and distinct cultivar of *Viola* plant named 'SMEV1' as described and illustrated herein.

* * * * *